United States Patent [19]

Tsujiuchi et al.

[11] Patent Number: 4,895,431
[45] Date of Patent: Jan. 23, 1990

[54] METHOD OF PROCESSING ENDOSCOPIC IMAGES

[75] Inventors: Junpei Tsujiuchi; Nagaaki Ohyama, both of Kawasaki; Toshio Honda, Yokohama; Eric Badique, Tokyo; Susumu Kikuchi, Hachioji, all of Japan

[73] Assignee: Olympus Optical Co., Ltd., Tokyo, Japan

[21] Appl. No.: 119,784

[22] Filed: Nov. 10, 1987

[30] Foreign Application Priority Data

Nov. 13, 1986 [JP] Japan ................................ 61-270038
Jul. 8, 1987 [JP] Japan ................................ 62-168791

[51] Int. Cl.$^4$ ........................ G02B 27/00; G02B 27/46
[52] U.S. Cl. .................................... 350/320; 350/321; 350/162.13; 350/3.82; 128/4; 342/64; 358/125; 356/390; 364/822
[58] Field of Search ................. 350/320, 321, 3.77, 350/3.68, 3.82, 162.12, 162.13; 356/347, 390, 397, 398; 128/4; 303.15; 358/125; 342/64; 364/822

[56] References Cited

U.S. PATENT DOCUMENTS

| | | | |
|---|---|---|---|
| 3,507,549 | 4/1970 | Land | 350/320 |
| 4,094,011 | 6/1978 | Nagao | 350/3.82 |
| 4,174,179 | 11/1979 | Tschudi et al. | 350/3.77 |
| 4,637,056 | 1/1987 | Sherman et al. | 350/162.13 |
| 4,669,054 | 5/1987 | Schlunt et al. | 350/162.13 |
| 4,697,210 | 9/1987 | Toyota et al. | 128/4 |
| 4,702,229 | 10/1987 | Zobel | 128/4 |

FOREIGN PATENT DOCUMENTS 3412533 10/1985 Fed. Rep. of Germany .

*Primary Examiner*—Bruce Y. Arnold
*Assistant Examiner*—Loha Ben
*Attorney, Agent, or Firm*—Stevens, Davis, Miller & Mosher

[57] ABSTRACT

A method of processing images taken by an endoscope having insertion section, bending section and operation section including a step of entering a first image of an object taken by the endoscope having the bending section situated in a first position, a step of entering a second image taken by the endoscope having the bending section situated in a second position, after moving the bending section into the second position by operating an operation member, the first image being partially overlapped with the second image, a step of detecting a positional relation between the first and second positions by detecting the movement of the bending section, a step of deriving a distance between corresponding points on the first and second images, a step of deriving three dimensional information of the object, and a step of displaying a three dimensional image of the object in accordance with the three dimensional information.

34 Claims, 22 Drawing Sheets

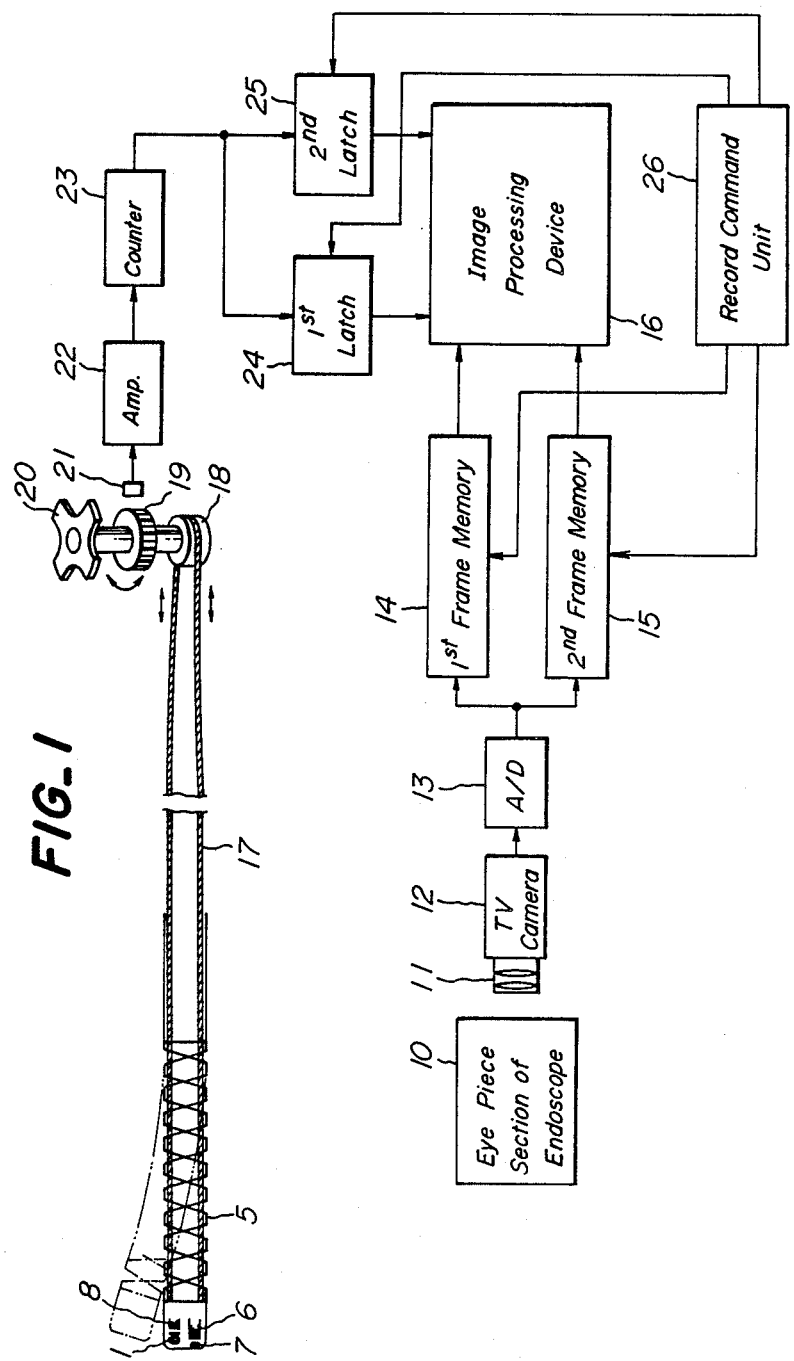

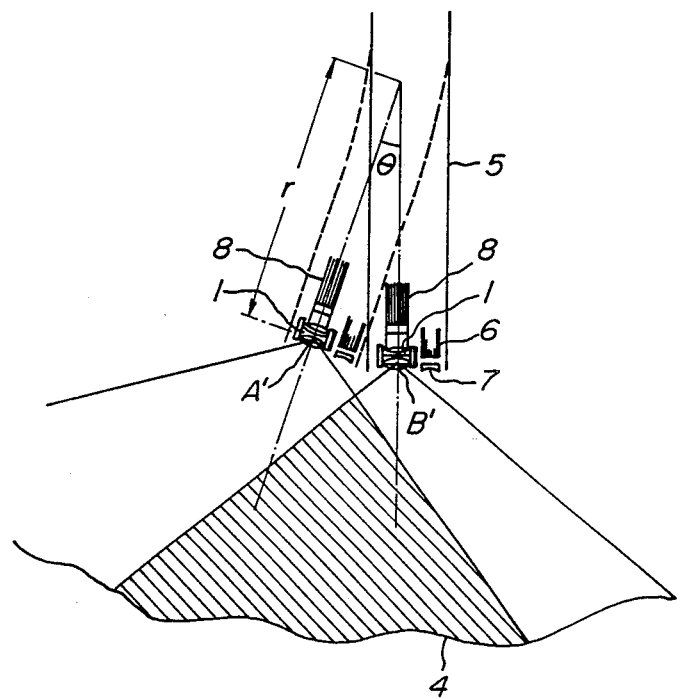
FIG_2

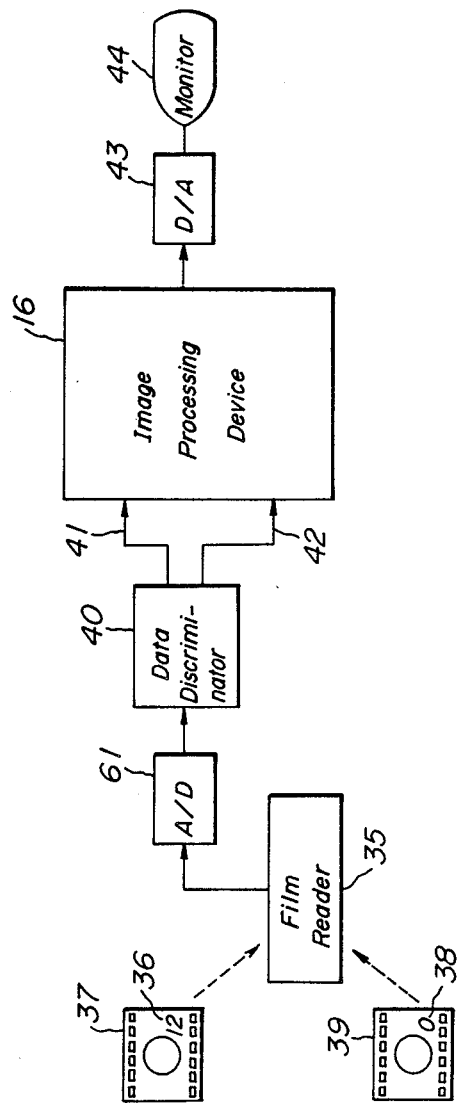

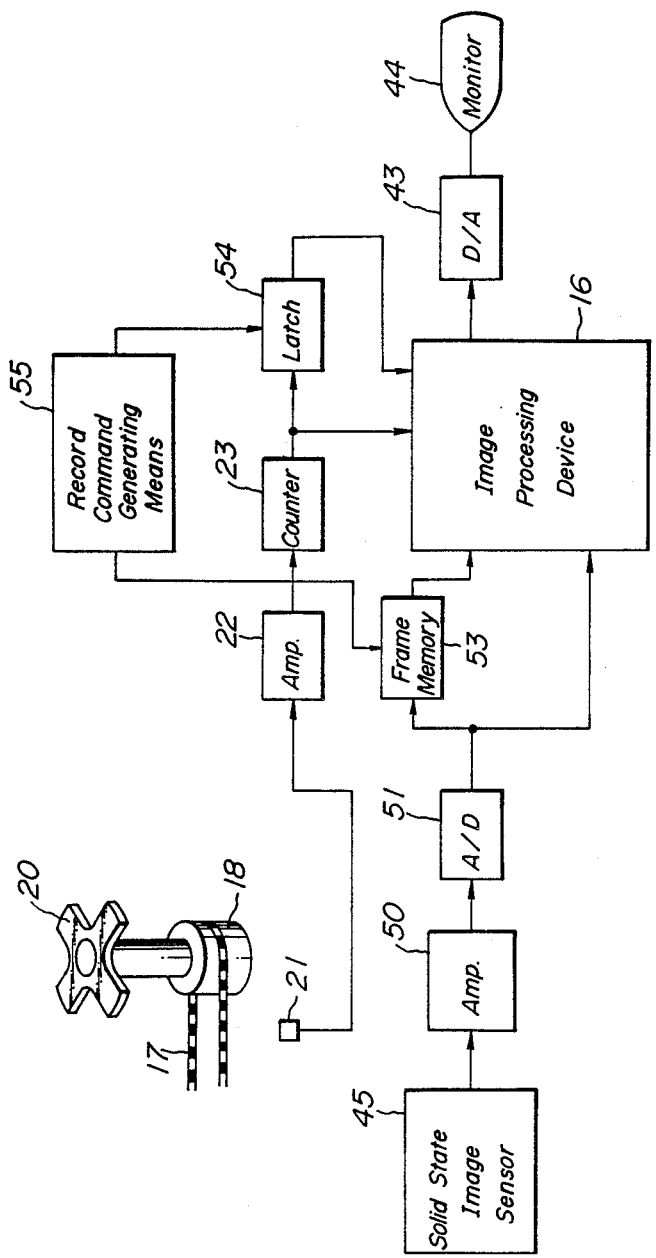
FIG._5

FIG_6
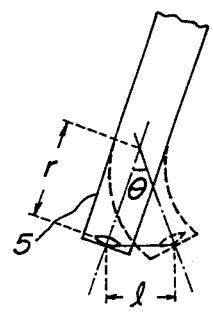
FIG_7
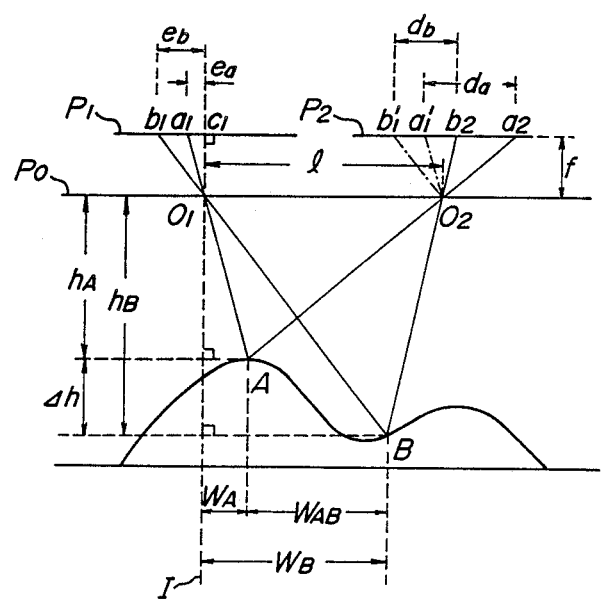

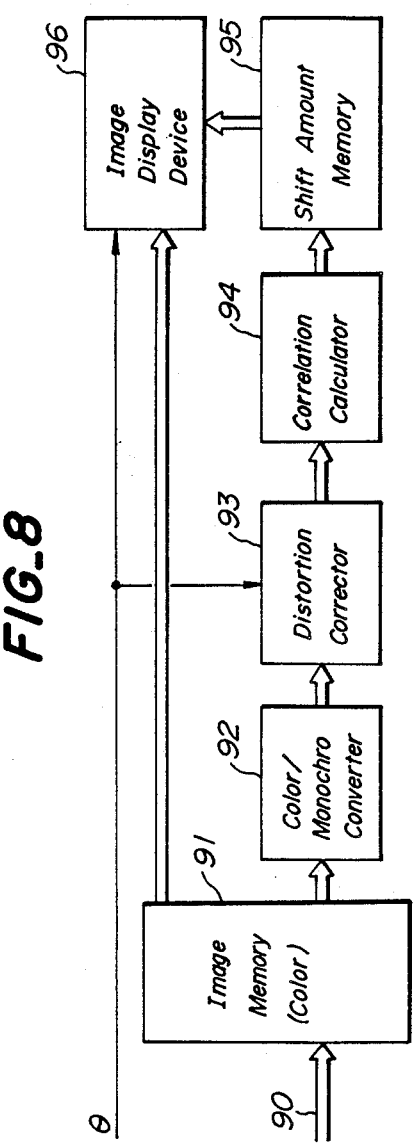
FIG_8
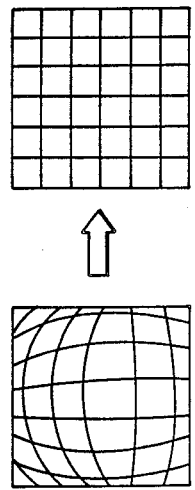
FIG_9

FIG_10
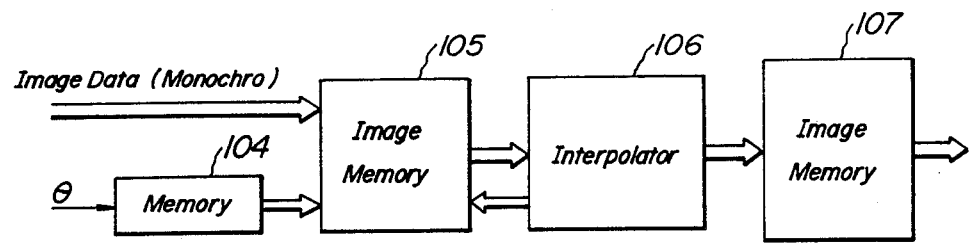
FIG_11
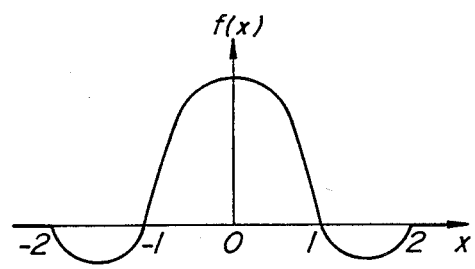

FIG_12
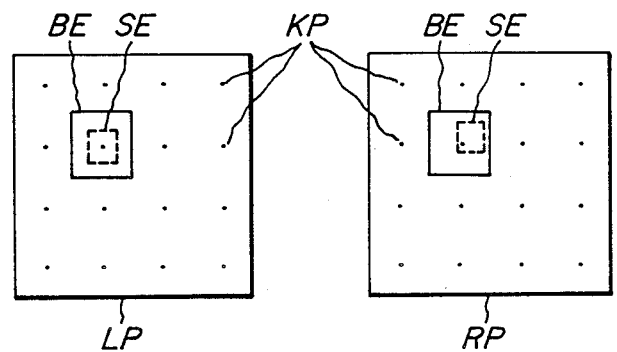
FIG_13
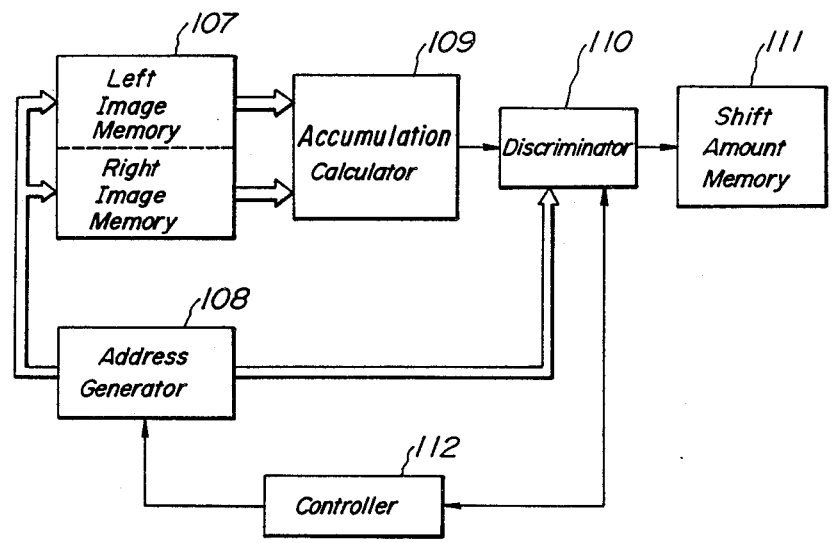

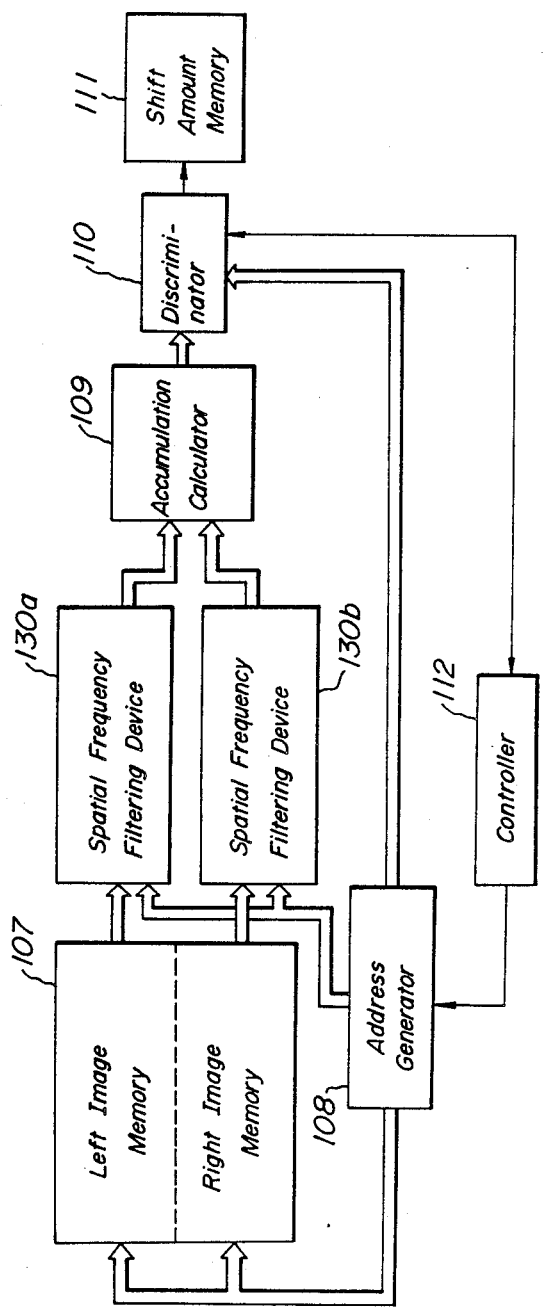
FIG_16

FIG_17
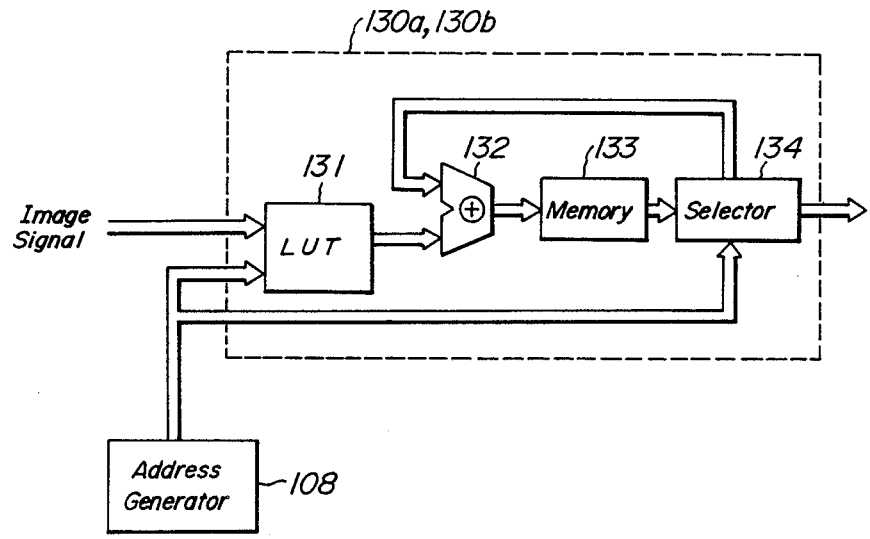
FIG_18
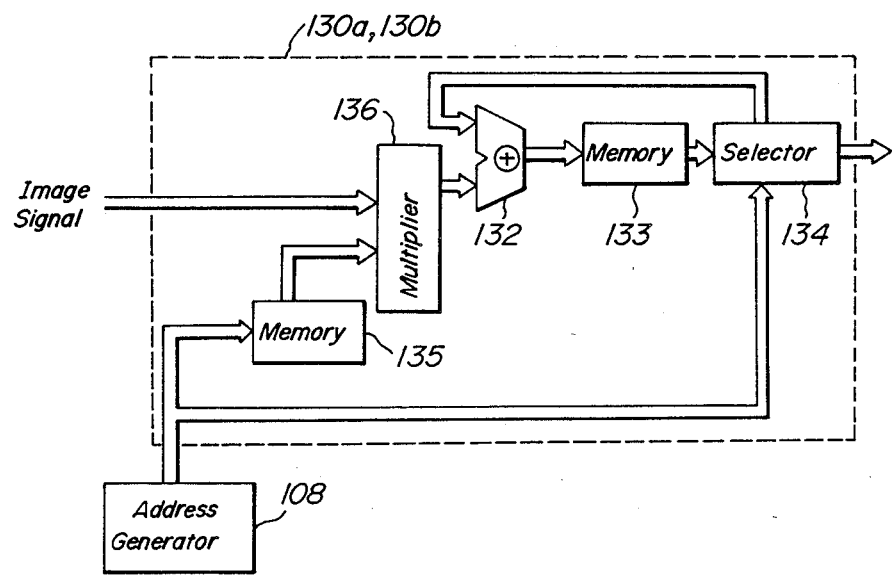

FIG_21
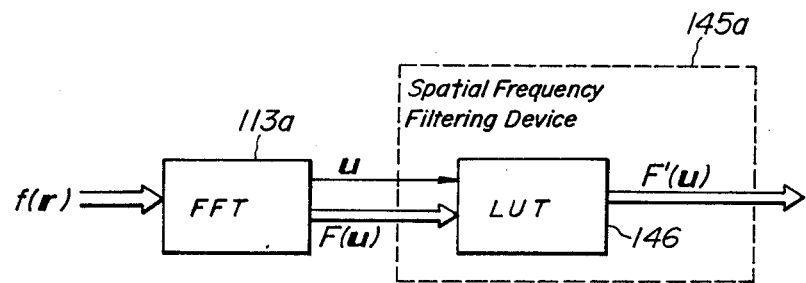
FIG_22
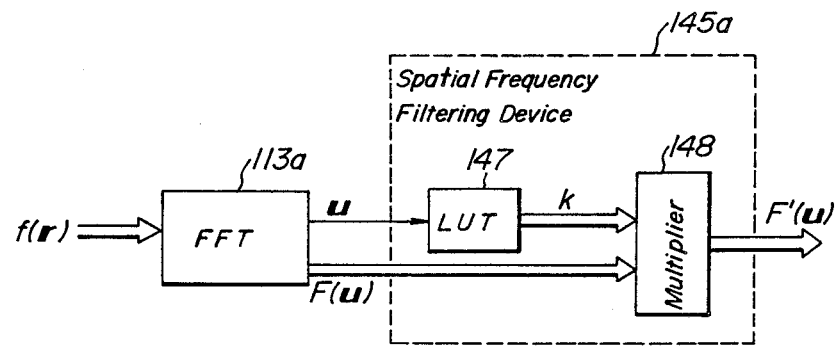

FIG_25
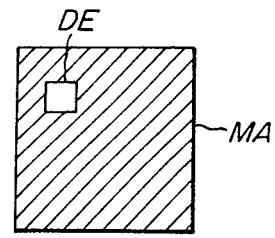
FIG_26
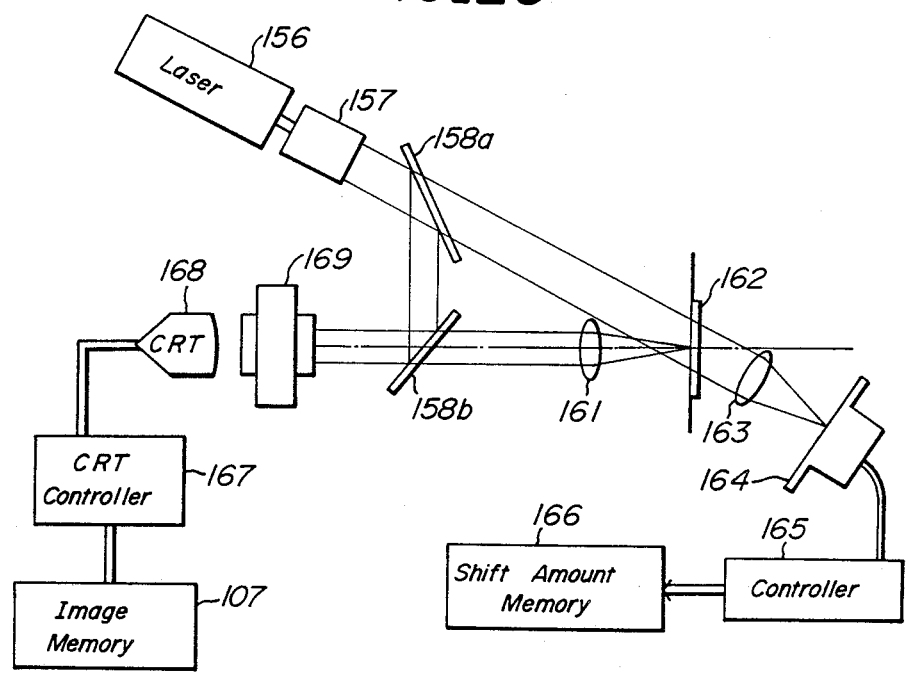

FIG_27
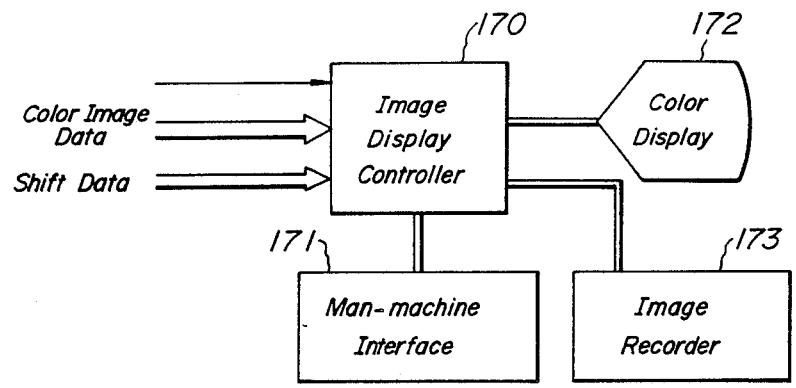
FIG_28A  FIG_28B  FIG_28C
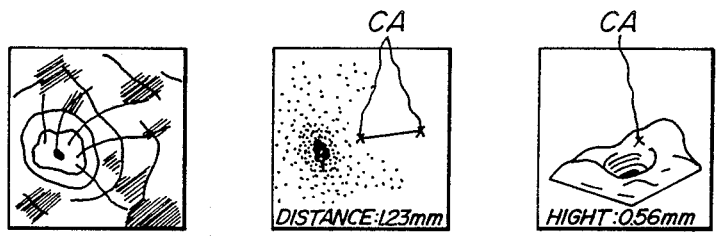

METHOD OF PROCESSING ENDOSCOPIC IMAGES

BACKGROUND OF THE INVENTION

Field of the Invention and Related Art Statement

The present invention relates generally to a technique for processing images taken with the aid of an endoscope, and more particularly to a method of deriving three dimensional information from a plurality endoscopic images.

Heretofore, there have been proposed various types of endoscopes for taking images within a body and a mechanical construction. There are an optical endoscope comprising an image guide fiber bundle for transmitting an image from a distal end to a proximal end of the endoscope, and an electronic endoscope comprising a solid state image sensor arranged at the distal end of endoscope. With the aid of such endoscopes, images of objects within a body can be directly viewed. Further, when the endoscopic images are required to be recorded, a still camera is provided at an eyepiece section of endoscope and endoscopic images are recorded on photographic films, or an image signal supplied from the solid state image sensor is recorded in an image storing device such as a magnetic and optical image record devices.

In the known systems for recording the endoscopic images, endoscopic images are recorded independently from each other. In some cases a plurality of images are recorded successively, but any relation has not been detected or determined between these images. Therefore, in case of processing the recorded images, each image has to be processed separately. Therefore, in the known endoscopic image processing system, it is impossible to display a three-dimensional image of an object. It has been proposed to take stereoscopic images with the aid of the endoscope. To this end, there are arranged two objective lenses at the distal end of the endoscope and a pair of image guides within the insertion section. However, it is apparent that a size, particularly a diameter of such an endoscope is liable to be large. Further, the two objective lenses could not be arranged such that a sufficient parallax can be obtained, so that the stereoscopic effect could be achieved sufficiently. Due to the above mentioned drawbacks, the stereoscopic endoscope has not been practically manufactured and sold.

SUMMARY OF THE INVENTION

The present invention has for its object to provide a novel and useful method of processing a plurality of endoscopic images, while these images can be related to each other in accordance with a positional relation existing therebetween.

It is another object of the invention to provide a method of processing a plurality of endoscopic images, in which three dimensional information of an object is derived in accordance with a positional relation existing therebetween and a three dimensional image of the object can be displayed.

According to the invention a method of processing endoscopic images taken by an endoscope having an insertion section, a bending section provided at a distal end of the insertion section and an operation section for controlling a bending movement of the bending section, comprises:

entering a first endoscopic image of an object taken by the endoscope situated in a first position;

entering a second endoscopic image of the object taken by the endoscope situated in a second position; said second endoscopic image being at least partially overlapped with said first endoscopic image; and detecting a positional relation between said first and second positions of the endoscope.

According to the further aspect of the invention, a method of processing endoscopic images taken by an endoscope having an insertion section, a bending section provided at a distal end of the insertion section, and an operation section for controlling a bending movement of the bending section, comprises entering a first endoscopic image of an object taken by the endoscope in a first position;

entering a second endoscopic image of the object taken by the endoscope in a second position, said second endoscopic image being at least partially overlapped with said first endoscopic image;

detecting a positional relation between said first and second endoscopic images; and processing said first and second endoscopic images in accordance with said positional relation to derive geometric information of the object.

BRIEF DESCRIPTION OF THE DRAWINGS

FIG. 1 is a schematic view showing a first embodiment of the endoscopic image processing system according to the invention;

FIG. 2 is an enlarged view of a distal end of endoscope shown in FIG. 1;

FIGS. 3A and 3B are schematic views depicting a second embodiment of the system according to the invention;

FIG. 5 is a schematic view showing a fourth embodiment of the system according to the invention;

FIG. 6 is a schematic view explaining a shift amount of the distal end of endoscope;

FIG. 7 is a schematic view showing a measuring method in an image processing device in the first to fourth embodiments;

FIG. 8 is a block diagram of the image processing device;

FIG. 9 is a schematic view explaining how to correct the image distortion;

FIG. 10 is a block diagram illustrating the distortion corrector;

FIG. 11 is a graph depicting the b-spline function;

FIG. 12 is a schematic view explaining the operation of the correlation calculator;

FIG. 13 is a block diagram showing a first embodiment of the electronic correlation calculator;

FIGS. 14, 15 and 16 are block diagrams illustrating second, third and fourth embodiments of the electronic correlation calculator;

FIGS. 17, 18 and 19 are block diagrams showing first, second and third embodiments of the spatial frequency filtering device;

FIG. 21 is a block diagram illustrating an embodiment of the spatial frequency filtering device shown in FIG. 20;

FIG. 22 is a block diagram showing another embodiment of the spatial frequency filtering device;

FIG. 25 is a plan view illustrating the mask shown in FIG. 24;

FIG. 26 is a schematic view showing a second embodiment of the optical correlation calculator;

FIG. 27 is a block diagram of the image display device shown in FIG. 8;

FIGS. 28A, 28B and 28C are schematic plan views showing examples of display;

DESCRIPTION OF THE PREFERRED EMBODIMENTS

Figure 3A:
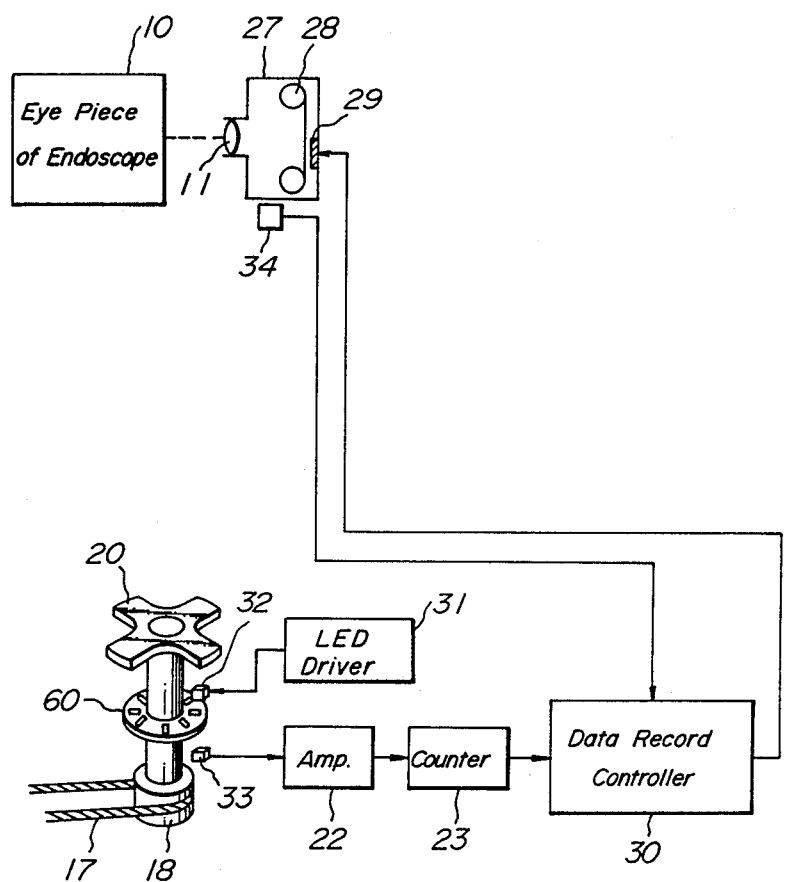

FIG. 1 is a schematic view showing a first embodiment of the endoscopic image processing system according to the invention. An objective lens 1 is provided in a distal end of a bending portion 5 of the endoscope. The objective lens 1 has a function to form an image of an object to be observed onto an end surface of an image guide 8 formed by an optical fiber bundle. In the distal end of the bending portion 5 there is also provided a concave or convex lens 7 which projects light transmitted through a light guide 6 made of, for instance an optical fiber bundle upon the object such that the object is illuminated uniformly. The proximal end of the endoscope is extended up to an eyepiece section 10 provided at a control section. Then the image of the object formed on the exit surface of the image guide 8 is picked up via an eyepiece (not shown) and imaging lens 11 by a television (TV) camera 12. An analog output image signal from the TV camera 12 is converted into a digital image signal with the aid of an analog-to-digital (A/D) converter 13. The digital image signal thus derived is stored in first or second frame memory 14 or 15. The image signal read out of the first and second frame memories 14 and 15 are supplied to an image processing device 16 which will be explained later.

An angle wire 17 for steering the bending section 5 into a desired direction extends in the endoscope and is wound around a rotating drum 18 provided in the control section. The rotating drum 18 is arranged in the control section coaxially with a pattern disc 19 and angle handle 20. Along the peripheral portion of pattern disc 19 are formed black and white equidistant pattern which is detected by a sensor 21 including a reflection type photosensor. An output signal from the sensor 21 is amplified by an amplifier 22 and is then supplied to a counter 23. An output signal of the counter 23 is supplied to first and second latches 24 and 25 and output signals from the latches are supplied to the image processing device 16. A record command unit 26 including operation switch, timing circuits, etc. supplies its output signal to the first and second frame memories 14, 15 and first and second latches 24 and 25.

Now the operation of the above system will be explained. In a first position of the bending section 5 shown by a solid line in FIG. 1 (in this position, the bending section is not bent), under the control of a command supplied from the record command unit 26, a digital image signal picked-up by the TV camera 12 is stored in the first frame memory 14. At the same time, a count value of the counter 23 is stored in the first latch 24. Then the angle handle 20 is rotated slightly and the bending section 5 of the endoscope is bent as illustrated by a broken line in FIGS. 1 and 2.

In conjunction with the rotation of the angle handle 20, the pattern disc 19 is rotated and the sensor 21 detects the black and white pattern change. This is to say, the pattern disc 19 and sensor 21 constitute a rotary encoder which generates an information signal representing an amount and a direction of rotation. This information signal is supplied to the counter 23 via the amplifier 22. In the second position of the bending section 5, the digital image is stored in the second frame memory 15. At the same time, the count value of the counter 23 is stored in the second latch 25. In this manner, there are stored in the first and second frame memories 14 and 15 two images of a part of the object 4 to be observed which have a parallax shown by A'-B' in FIG. 2, said part of the object 4 being adjacent to a hatched area, and at the same time the positional relation between these two images has been stored in the first and second latches 24 and 25.

The digital images are red out of the first and second frame memories 14 and 15 and are processed in the image processing device 16. The count values stored in the first and second latches 24 and 25 are also supplied to the image processing device 16 and are converted into angle information $\theta$. In the image processing device 16, various kinds of information such as a difference in heights between two points on the object 4 and projection and depression of the object by processing the signals in the manner which will be explained later.

Figure 4:
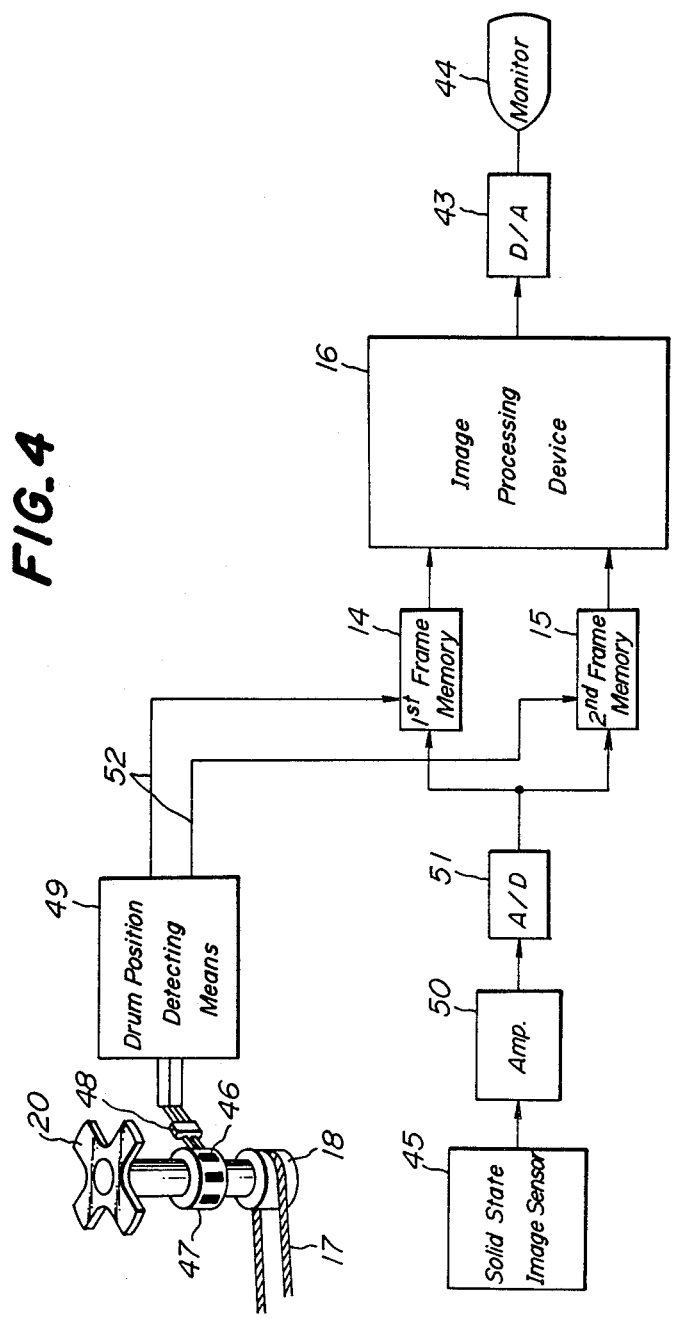
FIG. 4 is a schematic view illustrating a third embodiment of the system according to the invention.

In the present embodiment, use is made of the optical endoscope having the image guide, but use may be made of the video endoscope comprising the solid state image sensor arranged at the distal end of the endoscope. In such a case, the analog image signals produced by the solid state image sensor are converted into the digital image signals and then are stored in the first and second frame memories 14 and 15. This construction will be explained as a third embodiment (FIG. 4).

Now a second embodiment of the system according to the invention will be explained with reference to FIGS. 3A and 3B. As illustrated in FIG. 3A, in opposition to the eyepiece section 10 of the endoscope there is arranged a still camera 27 and the endoscopic image transmitted to the proximal end of the image guide is formed on a photographic film 28. In the camera 27 there is arranged a data image on the film 28. The data recording means 29 for forming a data image on the film 28. The data recording means 29 comprises an LED display and is connected to a data record controlling means 30. In the present embodiment, a slit disc 60 is coupled with the angle handle 20 and rotary drum 18. A light emitting diode (LED) 32 is driven by an LED driver 31, and light emitted from LED 32 is made incident upon a light receiving element 33 formed by phototransistor through slits formed in the slit disc 60. An output signal from the light receiving element 33 is supplied via an amplifier 22 to a counter 23 and a count value in the counter is supplied to the data record controlling means 30. A release command generating means 34 comprising release switch is also connected to the data record controlling means 30.

After the film 28 in the still camera 27 has been exposed to the endoscopic image, the film is developed. Then, as illustrated in FIG. 3B, the image formed on the developed film is read out by means of a film reading means 35. That is to say, a first slide 37 having the endoscopic image and position data 36 which represents the position of the bending section 5 of the endoscope and a second slide 39 including the endoscopic image and position data 38 of the bending section 5 are read out by the film reading means 35 comprising a drum type film scanner. An output signal from the film reading means 35 is supplied via an A/D converter 61 to a data discriminating means 40 which serves to discriminate the image data and the position data. The image data 41 and position data 42 are supplied to the image processing device 16. An output signal from the image processing device 16 is supplied via a D/A converter 43 to a monitor 44 comprising the television monitor.

Now the operation of the system according to the second embodiment will be explained. When the bending section 5 of the endoscope is in a first position (position represented by the solid line in FIG. 2), a release command is generated by operating the release command generating means 34, the count value of the counter 23 is recorded on the photographic film 28 by the data recording means 29 under the control of the data record controlling means 30. In this case, the count value is recorded as it is. It should be noted that the count value may be first encoded and an encoded pattern may be recorded on the film 28. Next, the film 28 is wound by one frame and the angle handle 20 is rotated so that the bending section 5 of the endoscope is brought into the second position shown by the dotted line in FIG. 2. The slit disc 60 is also rotated in conjunction with the angle handle 20 and the light receiving element 33 detects the light flux generated from LED 32 and interrupted by the slit disc 60. In this case, when two pairs of the combination of LED 32 and light receiving element 33 are arranged separately from each other by 90° with respect to the slit pattern, it is possible to detect not only the rotational amount, but also the rotational direction. Therefore, the count value in the counter 23 is also changed in accordance with the rotation of the slit disc 60. Then, the release operation is effected with the aid of the release command generating means 34, and the count value of the counter 23 is recorded on the film 28 by means of the data recording means 29 and data record controlling means 30. At the same time, the endoscopic image of the object is exposed on the photographic film 28. In the manner explained above, there are obtained the first and second slides 37 and 39 having the endoscopic images viewed from the two different positions of the bending section 5 and the information of these positions. The first and second slides 37 and 39 are set on the film reading means 35 and the output signal from the film reading means is converted into the digital signal by the A/D converter 61. The data discriminating means 40 discriminates the endoscopic image data 41 from the position data 42 which are then supplied to the image processing device 16.

The image processing device 16 effects calculations on the basis of the entered data to derive a distance to the object 4 and depressions and projections of the object. These calculated results are supplied to the monitor 44 via the D/A converter 43 to display three-dimensional images on the monitor screen.

FIG. 4 is a schematic view depicting a third embodiment of the system according to the invention. In this embodiment, the image guide 8, eyepiece section 10, imaging lens 11 and TV camera 12 in the embodiment shown in FIG. 1 is replaced by a solid state image sensor 45 arranged in the distal end of the endoscope. That is to say, the endoscope of the present embodiment is formed as the video endoscope. The objective lens not shown is provided at the distal end of the endoscope such that an image of the object is formed on the solid state image sensor 45. An output signal from the solid state image sensor 45 is supplied via a video amplifier 50 to an A/D converter 51. A pattern disc 47 having a conductive pattern 46 is coupled with the angle handle 20 and a contact brush unit 48 for detecting the pattern 46 is provided. The brush unit 48 is connected to a drum position detecting means 49. The brush unit 48 comprises three sets of brushes in order to detect the rotational direction as well as the rotational angle. These three sets of brushes are deviated from each other in the rotational direction so that the rotational direction can be detected in accordance with the order of two sets of brushes which are short-circuited by the conductive pattern of the pattern disc 47. The drum position detecting means 49 supplies a record command signal 52 to first and second frame memories 14 and 15.

Now the operation of the system of the third embodiment will be explained. During the rotation of the angle handle 20, each time two sets of brushes in the brush unit 48 are short-circuited via a conductive pattern, the drum position detecting means 49 send the record command signal 52 to the first or second frame memory 14 or 15 so that the image signal derived from the solid state image sensor 45 is stored in the first or second frame memory. The first and second frame memories 14 and 15 are selected in an alternate manner. In this manner, in the first and second frame memories 14 and 15 there are stored two endoscopic images of the object viewed with a given parallax. The image signals read out of the frame memories 14 and 15 are supplied to the image processing device 16 which then derives various kinds of information about the object such as a distance to the object and depressions and protrusions of object. The thus derived information signal is displayed on the monitor 44 via D/A converter 43.

Now a fourth embodiment of the system according to the invention will be explained with reference to FIG. 5. In the fourth embodiment, the endoscope is formed as the video endoscope having the solid state image sensor provided at the distal end of the endoscope. An output signal from the solid state image sensor 45 is supplied via video amplifier 50 and A/D converter 51 to the image processing device 16. In order to detect the position of the bending section 5 of the endoscope, i.e. in order to derive the parallax, the angle wire 17 has black and white stripe pattern and amount of movement of the wire is detected by a sensor 21 comprising a reflection type photosensor. An output signal from the sensor 21 is supplied via an amplifier 22 to a counter 23 and a count value of the counter is supplied to a latch 54 and the image processing device 16. Further, there is provided a record command generating means 55 which is driven by an operation switch not shown to supply a driving signal to the frame memory 53 and latch 54.

Now the operation of the fourth embodiment will be explained. In this embodiment, the image signal is processed by the image processing device 16 which comprises the frame memory and latch and has a high operation speed. This is to say, during the bending section 5 being in the first position, the count value of the counter 23 is stored in the latch 54 in response to the record command generated from the record command generating means 55, and at the same time the endoscopic image signal derived by the solid state image sensor 45 is stored in the frame memory 53. When the bending section 5 of the endoscope is in the second position, the endoscopic image signal and the count value are directly supplied to the image processing device 16. Then the image processing device 16 can derive the distance to the object and the condition of depressions and protrusions of the object in a real time manner by utilizing the signals stored in the latch 54 and frame memory 53. The calculated data is displayed on the monitor 44 via D/A converter 43.

Now the operation of the image processing device 16 will be explained by taking an example for deriving the information which represents absolute values of heights and magnitudes of the object.

As illustrated in FIG. 6, the bending section 5 of the endoscope is bent by an angle $\theta$ and has a radius of curvature r. Since the angle $\theta$ is sufficiently small, a distance l of the objective lens positions before and after the bending, can be approximately expressed by $r \cdot \theta$, i.e. $l = r \cdot \theta$.

FIG. 7 is a schematic view showing a geometric relation between the two images and object. For the sake of simplicity, the optical axis of the objective lens 1 is in a plane perpendicular to a line connecting lens centers $O_1$ and $O_2$ before and after the movement. Now it is assumed that the two endoscopic images obtained at the two positions are denoted by $P_1$ and $P_2$ and a focal length of the objective lens 1 is f. Points A and B on the object are formed at points $a_1$ and $b_1$ on the image $P_1$ and at points $a_2$ and $b_2$ on the image $P_2$. Therefore, if the two images $P_1$ and $P_2$ are superimposed, the points $a_1$ and $b_1$ are positioned at points $a'_1$ and $b'_1$ on the image $P_2$. A distance between the points $a'_1$ and $a_2$ is expressed by $d_a$ and a distance between the points $b'_1$ and $b_2$ is denoted by $d_b$. Further a distance between the point A on the object and a plane $P_o$ which contains the centers $O_1$ and $O_2$ and is in parallel with the object is represented by $h_A$, and a distance between the point B and the plane $P_o$ is denoted by $h_B$. Then, there is obtained the following relation between $h_A$ and $d_a$ due to the similarity of a triangle $AO_1O_2$ and a triangle $O_2a'_1a_2$.

$$\frac{h_A}{l} = \frac{f}{d_a} \quad (1)$$

Therefore, $h_A$ is given by the following equation.

$$h_A = \frac{f \cdot l}{d_a} = \frac{f \cdot r \cdot \theta}{d_a} \quad (2)$$

Similarly $h_B$ is given by the following equation.

$$h_B = \frac{f \cdot l}{d_b} = \frac{f \cdot r \cdot \theta}{d_b} \quad (3)$$

In this manner, it is possible to derive an absolute height h at a point by calculating a distance d between corresponding points on the two images $P_1$ and $P_2$.

Next, a manner of calculating an absolute value of the distance between two points will be explained. Now it is assumed that a distance between a center $C_1$ of the image $P_1$ and $a_1$ is expressed by $e_a$ and a distance between $C_1$ and $b_1$ is denoted by $e_b$, and further distances from A and B to a line l which passes through $O_1$ and is perpendicular to the object are expressed by $W_A$ and $W_B$, respectively. Then, the following linear relation is obtained between $W_A$ and $e_a$.

$$\frac{W_A}{h_A} = \frac{e_a}{f} \quad (4)$$

Now, when the equation (2) is replaced in the equation (4), $W_A$ can be derived by the following equation (5).

$$W_A = \frac{e_a \cdot h_A}{f} = \frac{e_a \cdot f \cdot r \cdot \theta}{f \cdot d_a} = \frac{e_a \cdot r \cdot \theta}{d_a} \quad (5)$$

Similarly, $W_B$ is calculated as follows.

$$W_B = \frac{e_b \cdot r \cdot \theta}{d_b} \quad (6)$$

Therefore, a distance $W_{AB}$ between points of projection of the points A and B on the plane $P_o$ parallel to the object can be derived by the following equation.

$$W_{AB} = W_B - W_A = r \cdot \theta \left( \frac{e_b}{d_b} - \frac{e_a}{d_a} \right) \quad (7)$$

In the manner explained above, it is possible to derive an absolute magnitude of a distance between any two points on the image $P_1$.

Next, a manner of deriving a distance d between corresponding points on the two images $P_1$ and $P_2$ will be explained. This method is based on the examination of correlation in a small region in the two images. It is now assumed that small regions in the two images are expressed by f(r) and g(r) which are separated from each other by a distance D. That is to say, $g(r) = f(r - D)$ is satisfied. In the above notations, r represent coordinates in a two dimensional plane. Then, the correlation between f(r) and g(r) may be expressed as follows.

$$\Psi(s) = \int_A f(r) \cdot g^*(r-s) \cdot dr \quad (8)$$

In the following explanation, $\Psi(s)$ is expressed by $\Psi(s) = f(r) * g(r)$. When the above equation (8) is Fourier transformed, the following equation (9) may be obtained.

$$\Phi(u) = F(u) \cdot G^*(u) \quad (9)$$

In the equation (9), F(u) is the Fourier transformed equation of f(r) and G(u) is the Fourier transformed equation of g(r). Since $g(r) = f(r-D)$, the equation (9) may be rewritten into the following equation $$\Phi(u) = F(u) \cdot F^*(u) \cdot e^{-j2\pi u \cdot D} \quad (10)$$

When the equation (10) is inverse Fourier transformed, the following equation is derived.

$$\Psi(s) = R_{ff}(t) * \delta(t-D) \quad (11)$$

In this equation, $R_{ff}(t)$ is an autocorrelation function of f(r), and can be expressed as follows.

$$R_{ff}(t) = f(r) * f(r) \quad (12)$$

Further, $\delta(t-D)$ is the inverse Fourier transformation of $e^{-j2\pi u \cdot D}$. The equation (11) represents that the function $\Psi(s)$ has a peak at $s = D$. Therefore, by deriving the correlation function $\Psi(s)$ and detecting its peak position D, it is possible to determine an amount by which g(r) is shifted with respect to f(r). In this manner the distance d between corresponding points can be detected by deriving the correlation of the corresponding small regions selected from the two images $P_1$ and $P_2$.

Now the detailed construction of the image processing device 16 will be explained.

FIG. 8 is a block diagram illustration the whole construction of the signal processing system of the image processing device 16. The two color image data 90 sent from the endoscope is stored in an image memory 91. The image data read out of the image memory 91 is supplied to a color/monochrome converter 92 and is converted into monochrome image data which is suitable for measurement. The output signal from the color/monochrome converter 92 is supplied to a distortion corrector 93 and any distortion of the image is corrected thereby. Then the image data is supplied to a correlation calculator 94 and a distance between the corresponding points, i.e. the shift amount is calculated. The calculated shift amount is stored in a shift amount memory 95. The image data read out of the image memory 91, the shift amount read out of the memory 95 and the depression and protrusion information of the object calculated from $\theta$ are supplied to an image display device 96 and absolute values of magnitude and height of a portion in the image are displayed thereon.

(1) Image Entry

The two color image data picked-up by bending the bending section of the endoscope is stored in the image memory 91. The bending angle $\theta$ is entered in the distortion corrector 93 and image display device 96.

(2) Correction of Distortion of Image

The entered image is generally distorted owning to the reason that the objective lens 1 has a very wide viewing angle and the distal end of endoscope is tilted. The distortion has to be corrected. Before picking up the image of object, a standard panel having a number of squares is imaged under the same condition, and correction values are predetermined for each picture elements such that the distorted image can be corrected as illustrated in FIG. 9. Then the distortion of actually picked up endoscopic images is corrected by using said predetermined correction values.

FIG. 10 is a block diagram illustrating the construction of the distortion corrector 94. The value of $\theta$ is supplied to a memory 104 which stores correction values for all possible values of $\theta$. The correction values read out of the memory 104 are supplied to an image memory 105 as address signals under control of which the monochromatic image signal is stored in the image memory 105 at such locations that any distortions in the input image can be corrected.

Then, the interpolation is effected for the distortion free image read out of the image memory 105, so that the deterioration of high frequency components due to the distortion correction is compensated for.

The interpolation is carried out by using b-spline function similar to the well-known sinc function. The b-spline function illustrated in FIG. 11 is expressed as follows.

$$\begin{cases} f(x) = |x|^3 - 2|x|^2 + 1 \ldots |x| < 1 \\ f(x) = -|x|^3 + 5|x|^2 - 8|x| + 4 \ldots 1 \leq |x| < 2 \\ f(x) = 0 \ldots |x| \geq 2 \end{cases}$$

(3) Calculation of Correlation

In the calculation of correlation, in right and left images RP and LP shown in FIG. 12 there are defined detection points KP and calculation regions each having a center at a detection point. At first there are defined relatively large regions BE having a relatively small peak in correlation, and then small regions SE having a large peak in correlation is set in the regions BE. In this manner, the correlation can be calculated in an accurate and prompt manner.

Now several embodiments of the correlation calculator realized by electronic circuits will be explained.

Embodiment 1

FIG. 13 is a block diagram showing a first embodiment of the electronic correlation calculator. The calculator comprises image memory 107, address generator 108 and accumulation calculator 109. A calculation region for the image memory 107 is defined by the address generator 108 and the correlation is calculated by the accumulation calculator 109. The calculated result is judged by a discriminator 110. At first a large region BE is set by the address generator and if a calculated correlation exceeds a predetermined threshold value, the correlation value and corresponding address are sent to a controller 112.

The controller 112 controls under the correlation value and address the address generator 108 such that it generates addresses denoting small regions SE. Then the correlation is calculated for the small regions SE. The discriminator 110 detects the maximum value of the correlation and its address. The address thus detected is stored in a shift amount memory 111. The first embodiment of the correlation calculator can be constructed by simple parts, but the calculation time is rather long.

Embodiment 2

Figure 14:
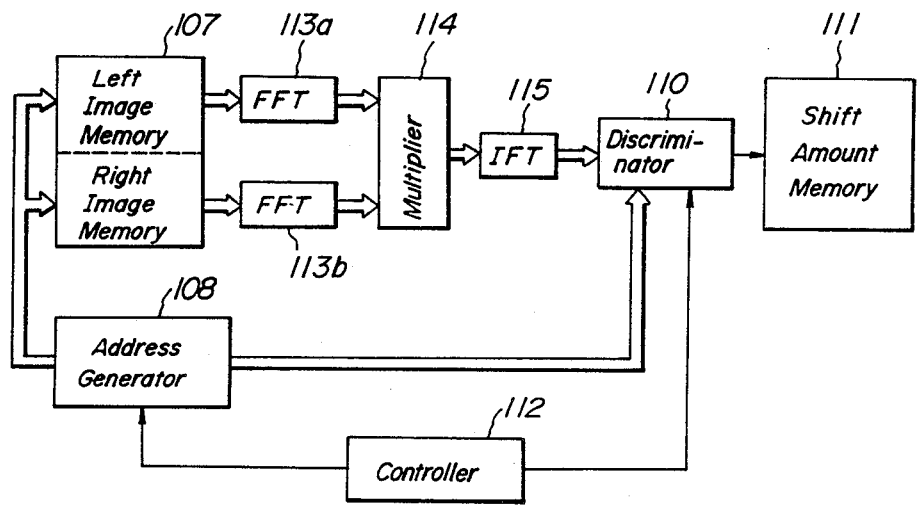

FIG. 14 is a block diagram illustrating a second embodiment of the electronic correlation calculator. In this embodiment, the accumulation calculator 109 of the first embodiment is replaced by FFTs (First Fourier Transformer) 113a, 113b, multiplier 114 and IFT (Inverse Fourier Transformer) 115. It should be noted that FFT 113b generates a value of conjugate of a complex number after the Fourier transformation. In the present embodiment the calculation can be carried out at a high speed.

Embodiment 3

Figure 15:
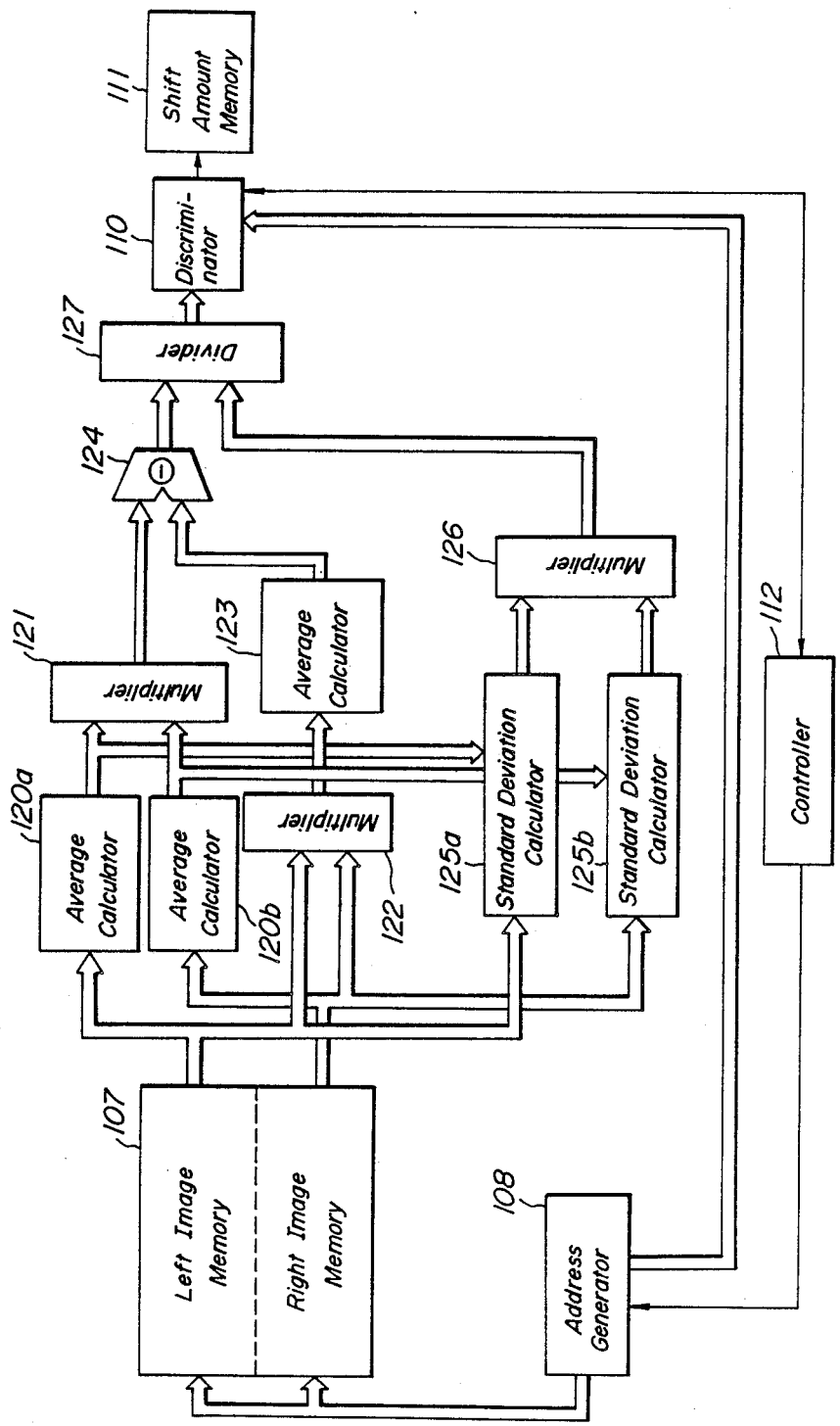

FIG. 15 is a block diagram depicting a third embodiment of the correlation calculator. Left and right image signals f and g stored in an image memory 107 are supplied to average calculators 120a and 120b and average densities e,ovs/f/ and e,ovs/g/ in given regions of the images are calculated. These average densities e,ovs/f/ and e,ovs/g/ are then supplied to a multiplier 121 to derive a product e,ovs/f/ ·e,ovs/g/ . The left and right image signals f and g are also supplied to a multiplier 122 to derive a product f·g which is then supplied to an average calculator 123 to derive an average of product $\overline{f \cdot g}$. The output signals e,ovs/f/ ·e,ovs/g/ from the multiplier 121 and output signal $\overline{f \cdot g}$ from the average calculator 123 are supplied to a subtracter 124 to derive a difference $\overline{f \cdot g} - e,ovs/f/ \cdot e,ovs/g/$. Further the left and right image signals f and g are supplied to standard deviation calculators 125a and 125b together with the average signals e,ovs/f/ and e,ovs/g/, respectively to derive the standard deviations of the left and right images, $\sigma_f = \sqrt{\overline{f^2} - (e,ovs/f/)^2}$ and $\sigma_g = \sqrt{\overline{g^2} - (e,ovs/g/)^2}$. Then these standard deviations $\sigma_f$ and $\sigma_g$ are supplied to a multiplier 126 to derive a product $\sigma_f \sigma_g$. The output signals of the subtracter 124 and multiplier 126 are supplied to a divider 127 to derive a quotient $(\overline{f \cdot g} - e,ovs/f/ \cdot e,ovs/g/)/(\sigma_f \sigma_g)$. The quotient thus calculated is supplied to a discriminator 110. In a manner similar to that of the previous embodiment, calculated correlation values for corresponding regions are judged to derive an address of correlation peak which is then stored in a shift amount memory 111.

In the present embodiment, the average values are subtracted from the left and right images and then the normalization is effected by using the standard deviations. That is to say, $$C = \frac{\overline{(f - \bar f) \cdot (g - \bar g)}}{\sigma_f \cdot \sigma_g} \tag{13}$$

is first calculated and then the above equation is rewritten into the following equation.

$$C = \frac{\overline{f \cdot g} - \bar f \cdot \bar g}{\sigma_f \cdot \sigma_g} \tag{14}$$

The circuit is constructed on the basis of the equation (14). Therefore, upon calculating the correlation value differences in gain and bias can be canceled out, so that the correlation can be detected precisely. In this manner the peak of the correlation can be detected accurately with the aid of the simple construction.

Embodiment 4

FIG. 16 is a block diagram illustrating a fourth embodiment of the correlation calculator. In this embodiment, the left and right image signals stored in an image memory 107 are supplied to spatial frequency filtering devices 130a and 130b, respectively.

Figure 19:
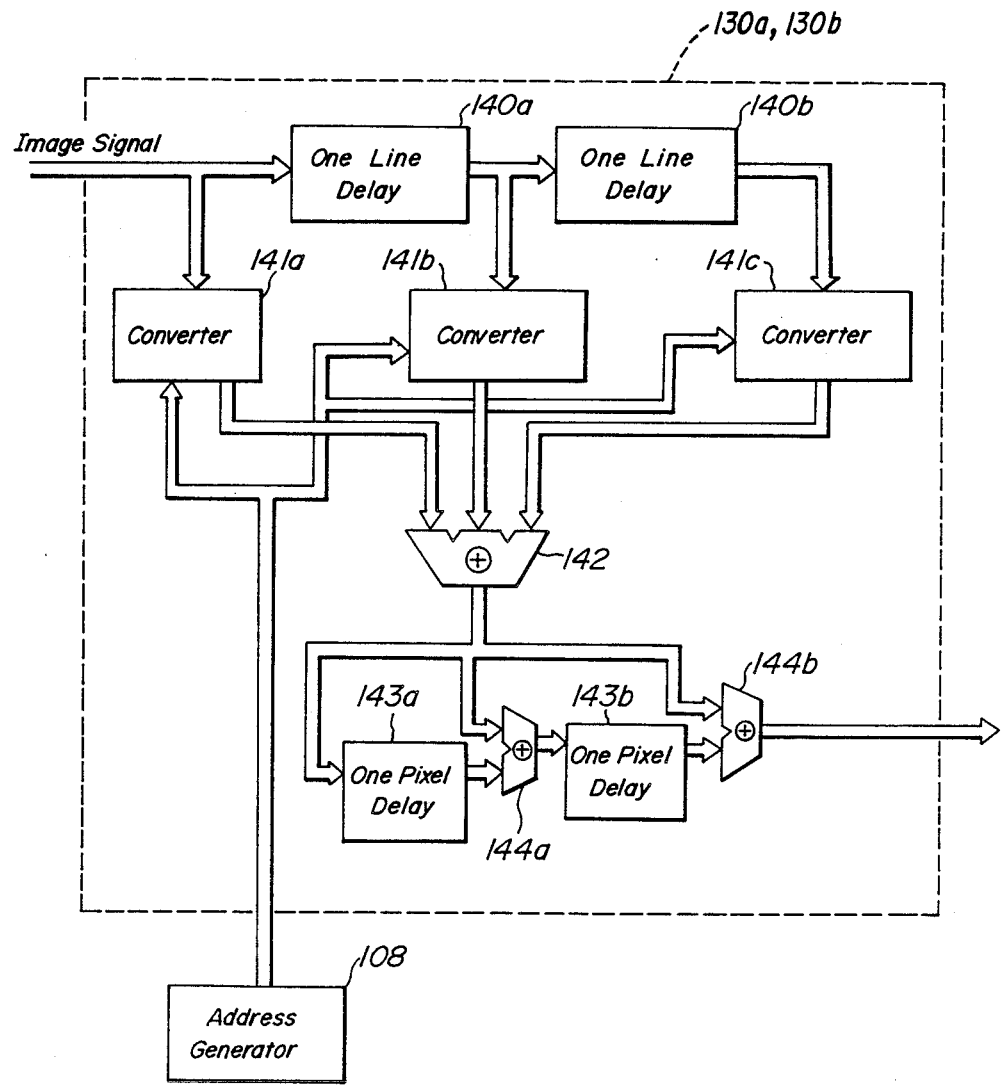

Output signals from the spatial frequency filtering devices 130a and 130b are then supplied to an accumulation calculator 109. The remaining construction is the same as the embodiment illustrated in FIG. 13. The spatial frequency filtering devices 130a, 130b may be constructed as shown in FIGS. 17, 18 and 19. In an embodiment shown in FIG. 17, the image signal read out of the image memory 107 and the address signal from the address generator 108 are supplied to a look-up table memory (LUT) 131 which generates a table conversion value in accordance with the image signal and address signal. The table conversion value is then added to a value stored in a memory 133 and an added value is stored in the memory 133 instead of the previously stored value in the memory 133. In this manner, an accumulation value for a given region in the image is calculated. The value read out of the memory 133 is selectively supplied to the adder 132 or to the accumulation calculator 109 with the aid of a selector 134 which is controlled by the address signal from the address generator 108.

In an embodiment depicted in FIG. 18, the LUT 131 in the embodiment shown in FIG. 17 is replaced by memory 135 and multiplier 136. The image signal is multiplied by coefficients corresponding to address values and multiplied values are supplied to the adder 132. The other construction is the same as that of the previous embodiment illustrated in FIG. 17.

FIG. 19 shows still another embodiment of the spatial frequency filtering device. In this embodiment, the operation for calculating the accumulated value for local regions of 3 pixel×3 pixel can be performed at a high speed. The image signal is supplied in a serial manner in the order of raster scanning. An image signal which has passed through two one-line delay devices 140a and 140b is supplied to a converter 141c, an image signal which has passed through the one-line delay device 140a is supplied to a converter 141b, and a non-delayed image signal is supplied to a converter 141a. The converters 141a~141c are constructed in a similar manner to the LUT 131 in FIG. 17 or the combination of the memory 135 and multiplier 136 in FIG. 18. The converter generates a converted value which is equal to the image signal multiplied by conversion coefficients corresponding to the addresses. The output signals from the converters 141a~141c are supplied to an adder 142, and an output signal from the adder 142 is supplied to one-pixel delay device 143a, adder 144a and one-pixel delay device 143b. The signal supplied to the one-pixel delay device 143a is delayed by a time period corresponding to one-pixel time and then is supplied to the adder 144a. In the adder 144a, the one-pixel delayed signal is added to the output signal from the adder 142 and an output signal from the adder 144a is further delayed by one-pixel time. The signal thus delayed is then added in the adder 144b to the signal from the adder 142. The output signal from the adder 144b is supplied as the accumulation value to the accumulation calculator 109. In the manner explained above, the accumulation value for the local area of 3×3 pixels can be calculated by a pipe line mode at a high speed. In the embodiment shown in FIG. 19, the local region has a dimension of 3×3 pixels, but when the number of pixels in the region is increased, it is possible to effect the accumulation calculation for a larger region.

As explained above, prior to effect the calculation for deriving the correlation in accordance with the accumulation calculation, each image is subjected to the spatial frequency filtering. The correlation of images may be derived accurately by extracting a region having a given spatial frequency component corresponding to characteristics of images. Therefore, in the above explained fourth embodiment, the spatial frequency filtering is carried out by effecting the calculation for deriving the accumulation for local regions having centers at pixels, and then the correlation is calculated. Since the movement of the distal end of endoscope is very small and the correlation between the right and left images is very large, the correlation can be derived accurately by extracting the high spatial frequency components in the image. For such a high pass filtering, the region of 3×3 pixels is processed by using the following Laplacian filter so that low frequency components are cut and edge portions are extracted.

| $P_1$ | $P_2$ | $P_3$ |     | 0  | −1 | 0  |                                   |
|-------|-------|-------|-----|----|----|----|-----------------------------------|
| $P_4$ | $P_0$ | $P_5$ | *   | −1 | 4  | −1 | = $4P_0 - (P_2 + P_4 + P_7 + P_5)$ |
| $P_6$ | $P_7$ | $P_8$ |     | 0  | −1 | 0  |                                   |

(image region)　　(coefficients)

In the above equation, the mark * represents the convolution.

If the correlation between the right and left images is deteriorated due to the distortion in shape due to geometric conditions and lighting conditions, the correlation value can be derived precisely by extracting lower spatial frequency components with the aid of a low pass filtering. The low pass filtering may be carried out by using the following averaging filter.

| $P_1$ | $P_2$ | $P_3$ |
|---|---|---|
| $P_4$ | $P_0$ | $P_5$ |
| $P_6$ | $P_7$ | $P_8$ |

*

| 1/9 | 1/9 | 1/9 |
|---|---|---|
| 1/9 | 1/9 | 1/9 |
| 1/9 | 1/9 | 1/9 |

$= 1/9 \sum_{i=0}^{8} P_i$

It should be noted that the accumulation calculation may be performed by using many other coefficients than those explained above and band pass filter for a particular spatial frequency filtering may be used by taking a large local area. That is to say, suitable filtering operations may be taken in accordance with the property of images to be processed.

In the above fourth embodiment, the correlation value can be calculated accurately by the simple construction.

Embodiment 5

Figure 20:
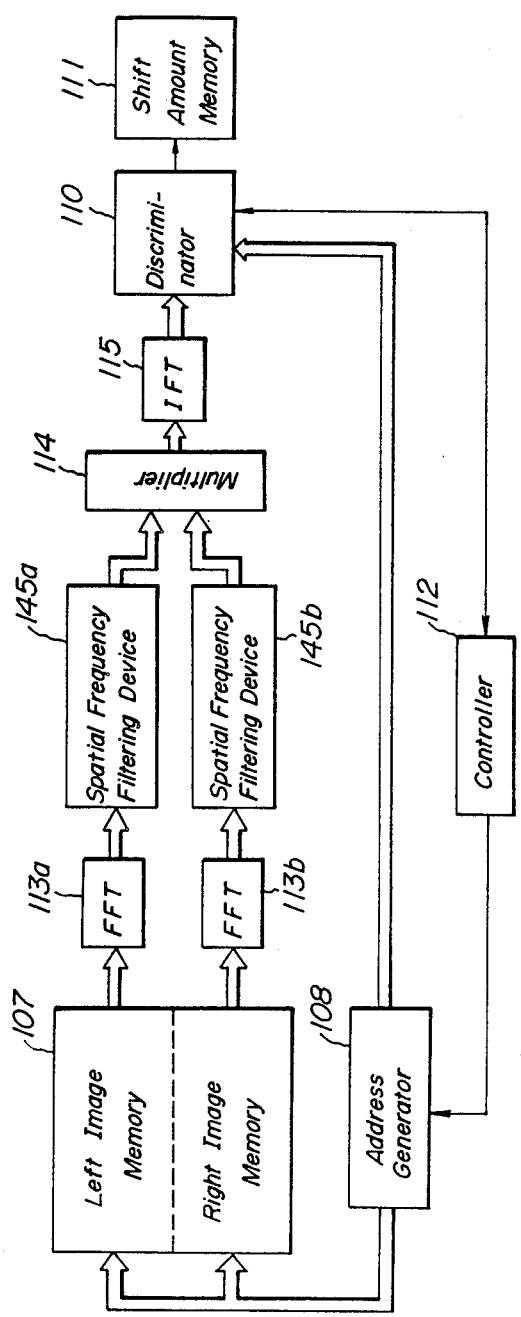
FIG. 20 is a block diagram showing a fifth embodiment of the electronic correlation calculator.

FIG. 20 is a block diagram showing the construction of a fifth embodiment of the correlation calculator. In the present embodiment, the output signals from FFTs 113a and 113b are passed through spatial frequency filtering devices 145a and 145b, respectively, and output signals from the filtering devices are supplied to the multiplier 114. Two embodiments of the spatial frequency filtering device are shown in FIGS. 21 and 22.

In the embodiment illustrated in FIG. 21, use is made of a look up table memory (LUT) 146. A frequency obtained by Fourier transforming the image signal f(r) and a Fourier transformed value F(r) are supplied from FFT 113a to LUT 146 and the conversion is effected in accordance with a conversion table selected by the entered frequency u to generate a result F'(u).

In the embodiment shown in FIG. 22, there are provided LUT 147 and multiplier 148. The frequency u is supplied from FFT 113a to LUT 147 to generate a coefficient k corresponding to the frequency u. F'(u) is derived by multiplying in the multiplier 148 the coefficient k with the Fourier transformed value F(u) supplied from the FFT 113a.

The other spatial frequency filtering device 145b may be equally constructed in the same manner.

Also in the fifth embodiment, the correlation value is calculated after effecting suitable spatial frequency filtering as in the fourth embodiment. However, since the filtering in the spatial frequency region is carried out after the Fourier transformation, it is possible to apply any desired filtering. That is to say, the filtering is not restricted by the size of the local regions, so that it is always possible to effect optimum filterings in accordance with property of images. Therefore, the more accurate calculation for deriving the correlation value can be performed at a high speed.

Embodiment 6

Figure 23:
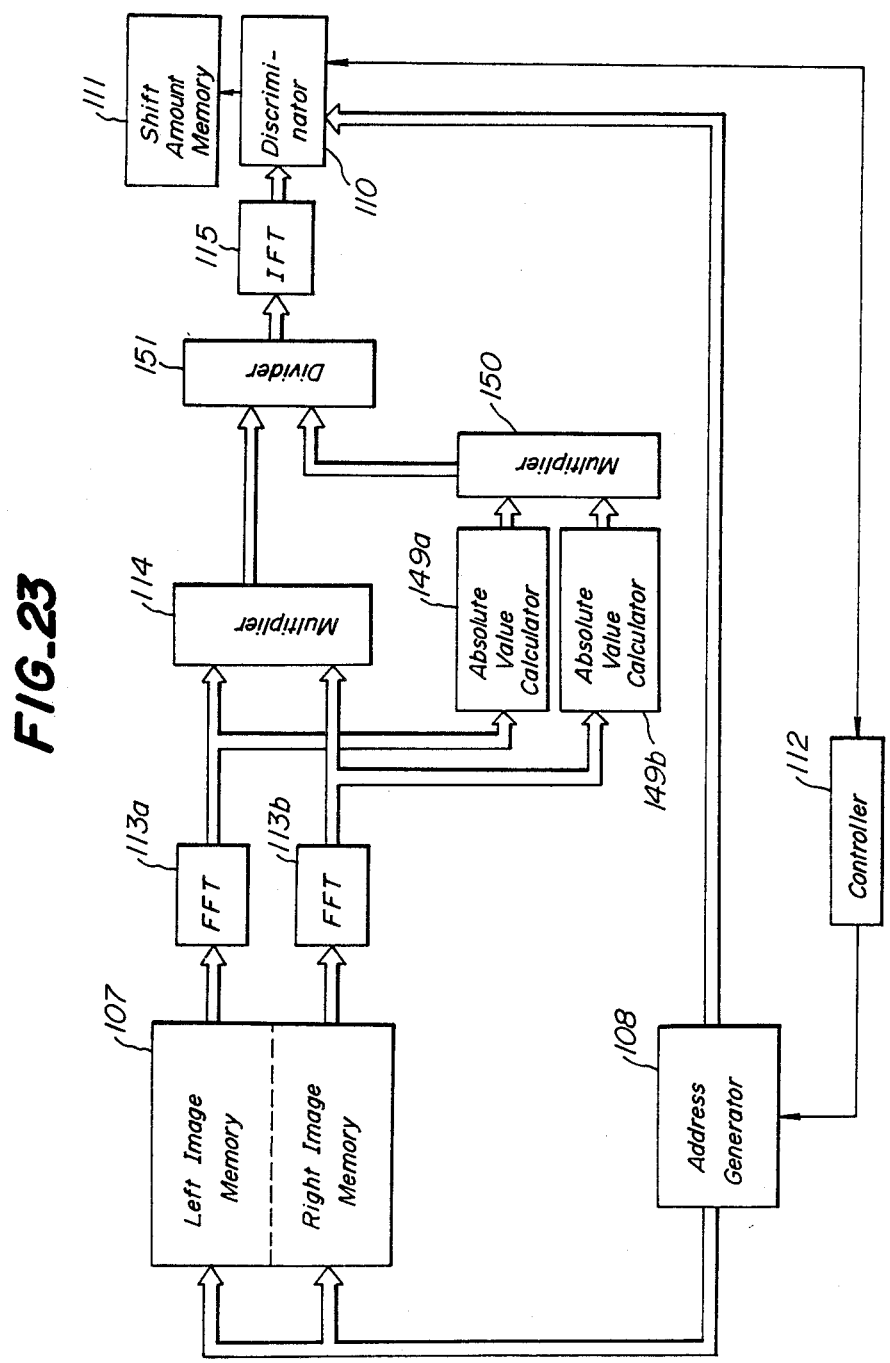
FIG. 23 is a block diagram depicting a sixth embodiment of the electronic correlation calculator.

FIG. 23 is a block diagram showing a sixth embodiment of the correlation calculator. The output signals from FFTs 113a and 113b are supplied not only to the multiplier 114, but also to absolute value calculators 149a and 149b, respectively. In the absolute value calculators 149a and 149b, absolute values of the Fourier transformed values ($|F| = \sqrt{F \cdot F^*}$) are calculated and then the absolute values are supplied to a multiplier 150. Next, output signals from the multipliers 114 and 150 are supplied to a divider 151 and a quotient derived from the divider is supplied to an inverse Fourier transformer 115. The remaining construction of this embodiment is same as that of the embodiment illustrated in FIG. 14.

In the sixth embodiment, the Fourier transformed values F and G* of the image f and g are divided by the absolute values $|F|$ and $|G|$, respectively and then the correlation value C is calculated. That is to say, the correlation value C is calculated by the following equation $$C = F^{-1}\left( \frac{F \cdot G^*}{|F||G|} \right) \quad (15)$$

F-1 means the inverse Fourier transformation.

In the sixth embodiment, the correlation can be determined without being dependent upon the Fourier spectrum and thus only the phase information determines the correlation. Therefore, the correlation value can be derived very accurately. In the endoscope, the angle of view of the objective lens is small and the bending angle of the distal end is small, so that the endoscopic image having the very high correlation are obtainable. Therefore the correlation value can be calculated in an accurate and prompt manner with the aid of the simple construction.

In the description so far explained, the correlation value is derived by the electronic circuit, but it is also possible to derive the correlation value by optical means. Now a few embodiments of the optical correlation calculator will be explained.

Embodiment 1

Figure 24:
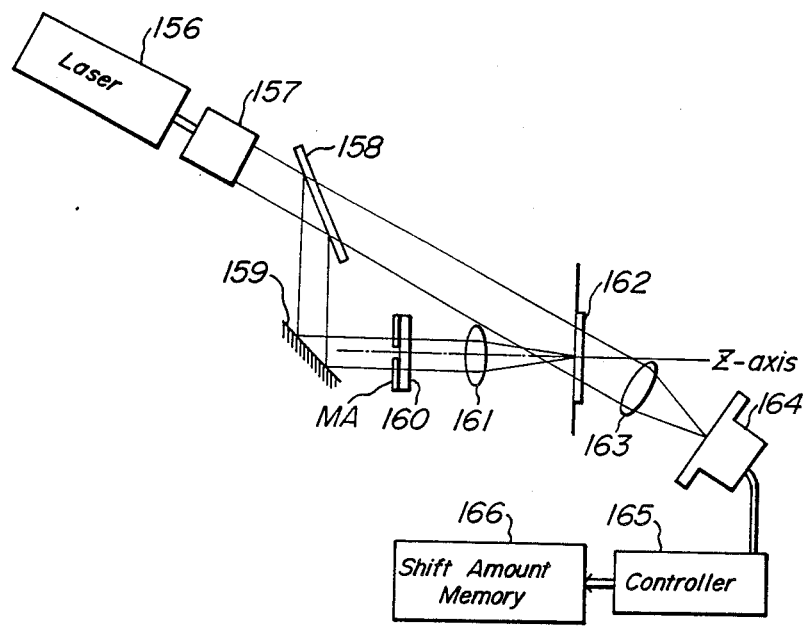
FIG. 24 is a schematic view showing a first embodiment of the optical correlation calculator.

FIG. 24 is a block diagram showing a first embodiment of the optical correlation calculator. An output laser beam from a laser 156 is widened by a beam expander 157 and then is partially transmitted through a half mirror 158 as a reference beam. A light flux reflected by the half mirror 158 is further reflected by a total reflection mirror 159 and is made incident upon an image film 160. The image film 160 is formed by a positive film having one of the right and left images stored in the image memory 107. As illustrated in FIG. 24, a mask MA is placed in front of the film 160 such that only a calculation object region DE (see FIG. 25) is exposed. Light transmitted through the image film 160 is collected by a lens 161 and is projected upon a photosensitive film 162 for forming a holographic film together with the reference light, photosensitive film 162 being positioned in a focal plane of the lens 161. Due to the interference between the image light and reference light there are produced fringes which are recorded on the photosensitive film 162. Then the image film 160 is exchanged by the other image film with a mask MA placed in front of the film such that only a calculation object region DE is exposed as shown in FIGS. 24 and 25. A position of a light spot is detected by a lens 163 and a detector 164 which can detect two dimensional distribution of the light intensity and arranged in a focal plane of the lens 163. In this manner, a controller 165 connected to the detector 164 can determine the spot position. The above explained operation is repeated, while the position of the mask is changed. In this manner, the shift amount can be derived and is stored in a shift amount memory 166.

Now the principle of the optical method of deriving the correlation value will be theoretically explained.

When a monochromatic plane wave transmitted through the image f(r) is collected by the lens, complex amplitude distribution $U_f(q)$ in the focal plane may be expressed by the following equation (16).

$$U_f(q) = \frac{A}{j\lambda f} \int \int_{-\infty}^{\infty} f(r) \exp\left[-j\frac{2\pi}{\lambda f} r \cdot q\right] dr \quad (16)$$

In the above equation, A represents an amplitude of the incident light and f denotes the focal length of the lens. In the equation (16), when it is assumed that a spatial frequency u=q/λf, the above equation represents the two dimensional Fourier transformation. Therefore, at the focal plane of the lens 161, there is formed the image which is the Fourier transformation of the image f(r). Then the intensity distribution of the interference between the Fourier transformed image and the reference light is recorded on the photosensitive film 162. In this case, the complex amplitude distribution $H_f(q)$ of light wave at the photosensitive film can be expressed as follows.

$$H_f(q) \alpha U_f(q) + A \exp(-jaq) \quad (17)$$

wherein $\alpha = 2n/\lambda \tan \beta$ and $\beta$ is an angle between the optical axis of the reference light and Z axis.

When it is assumed that the photosensitive material of the photosensitive film 162 has an amplitude transmittivity characteristic which is proportional to light intensity, the amplitude-transmittivity distribution $T_H(q)$ of the photosensitive film is represented by the following equation.

$$T_H(q) \alpha |U_f(q)|^2 = A^2 = AU_F(q)\exp(jaq) = AU_f^*(-q)\exp(-jaq) \quad (18)$$

Next, when the photosensitive film 162 which has been used to produce the holographic film is illuminated by light transmitted through a film 160 bearing the other image g(r), a wave plane O(q) of light transmitted through the photosensitive film 162 which has been used to produce the holographic film may be expressed as follows.

$$\begin{aligned}O(q) &\alpha U_g \cdot T_H(q) \\&= (|U_f(q)|^2 = A^2) \cdot U_g(q) = A \cdot U_f(q) \cdot U_g(q) \exp(=jaq) \\&= AU_f^*(q) \cdot U_g(q) \exp(-jaq)\end{aligned} \quad (19)$$

The lens 163 is arranged in a direction in which refracted light wave of the third term in the equation (19) is transmitted. By considering the two dimensional Fourier transformation of the lens 163, a complex amplitude distribution O'(r) in the focal plane of the lens 163 may be represented by the following equation (20).

$$O'(r) \alpha Af(r)^* g(r-\alpha) \quad (20)$$

If an origin is shifted to α, the equation (20) may be rewritten as follows.

$$O'(r) \alpha Af(r)^* g(r) \quad (21)$$

This equation is the same as the equation (8). Therefore, the two dimensional detector 164 is arranged in the focal plane of the lens 163 and a point having the maximum light intensity is detected. Then the shift amount between the images f(r) and g(r) can be detected.

When use is made of the optical correlation calculator, the correlation value can be derived instantaneously.

Embodiment 2

FIG. 26 is a schematic view showing a second embodiment of the optical correlation calculator. In this embodiment, the image read out of the image memory 107 and displayed on a CRT 168 via a CRT controller 167 is optically readout by an incoherent/coherent converter 169 using laser light. The incoherent/coherent converter 169 may be formed by LCLV or BSO using liquid crystal.

In the present embodiment, it is no more necessary to form the positive film and the conversion from the electric data to the optical data can be effected in a smooth manner.

(4) Image Display

FIG. 27 is a block diagram showing the construction of the image display device. In an image on display controller 170, input color image, shift amount and θ to be displayed are determined in accordance with commands supplied from a man/machine interface 171 comprising a keyboard and joymatic. The selected data is displayed on a color display 172. There are three display modes as illustrated in FIGS. 28A, 28B and 28C. In the first display mode, the input color image is displayed as it is as shown in FIG. 28A. In the second display mode, the depression and protrusion information is derived from the shift amount and θ is displayed as a gray image as illustrated in FIG. 28B. In the third display mode shown in FIG. 28C, the height information is displayed with the aid of three dimensional graphic display. The third display mode comprises two sub-modes. In the first sub-mode, the three dimensional image is represented by line images, and in the second sub-mode the color information is superimposed upon the three dimensional image. In the first sub-mode, the image display controller 170 effects the smoothing and less-sharpening processes, and in the second sub-mode the image display controller 170 effects the smoothing and shading processes so that the impression of three dimension may be enhanced.

It should be noted that in the third display mode, the three dimensional graphic display can be achieved from any angular direction in accordance with commands supplied from the man-machine interface 171.

In the second and third display modes, particular points on the image may be denoted by a cursor CA and the height, distance and area of the denoted portions may be displayed on the screen.

The image displayed on the color display 172 is recorded by an image recorder 173. The image recorder 173 may be formed by a still camera using a photographic film and instantaneously developed film, and a color hard copy machine.

The present invention is not restricted to the embodiments so far explained, but many modifications and alternations may be conceived by those skilled in the art within the scope of the invention.

The device for detecting the rotation of the pattern disc 19 in the first embodiment and the pattern belt 17 in the fourth embodiment may be formed by various kinds of sensors other than the optical sensor. For instance, the magnetic pattern may be detected by a magnetic/electric converting element such as hole element and magnetoresistance element. Further, the angle handle 20 may be rotated by an electric motor. Moreover, an amount of bending of the bending section may be detected by a strain gauge applied on the bending section 5 of the endoscope.

Figure 29:
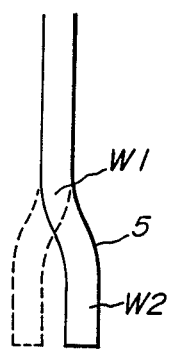
FIG. 29 is a cross sectional view showing another embodiment of the endoscope.
Figure 30:
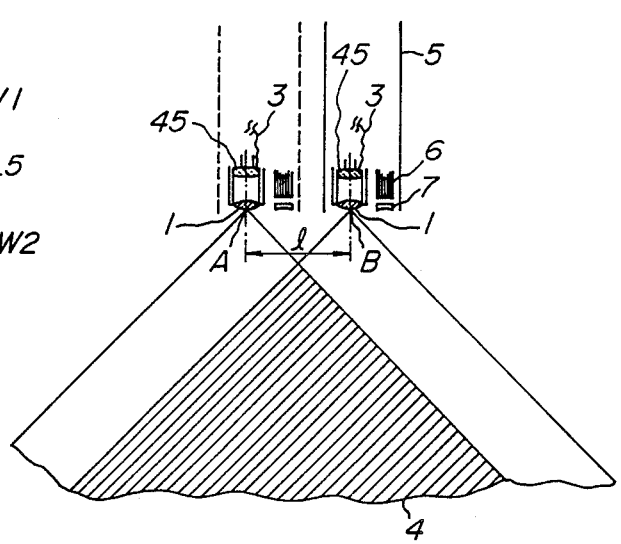
FIG. 30 is an enlarged view illustrating a distal end of the endoscope shown in FIG. 29.

In the first to fourth embodiments, the bending section 5 of the endoscope is bent at a single position, but it may be bent at two positions $W_1$ and $W_2$ as illustrated in FIG. 29. Then the objective lens 1 is shifted in such a manner that its optical axis is remained parallel to each other as shown in FIG. 30. In FIG. 30, a solid state image sensor 45 is arranged in the distal end of the endoscope such that an image of an object 4 is formed on the sensor by an objective lens 1. By taking two images while the optical axis of objective lens 1 is remained in parallel to each other, there is obtained a common field represented by hatchings, under a parallax of l.

In the above embodiment, the distal end of endoscope is curved, but it may be folded. Further the directions of bending or folding may be upper and lower directions, right and left directions, or a combination thereof.

In the first embodiment, the left and right images are stored in the first and second frame memories 14 and 15 and positions of the rotary drum 18 are stored in the first and second latches 24 and 25, but these signals may be stored in a single optical disc device or a magnetic disc device, and then the signals read out of the disc may be supplied to the image processing device 16.

Further, in the first embodiment, by deriving a difference between the count values stored in the first and second latches bending angle information is derived. This may be carried out either at the image processing device 16 or at the endoscope. Furthermore, if the count value of the counter 23 corresponds in an one-to-one manner to the bent position of the bending section 5, it is possible to enter information about the direction of the optical axis of objective lens. In such a case, the calculation may be performed much more accurately by taking into account of the direction of the optical axis of objective lens.

In the above explained first to fourth embodiments, the image signal supplied from the TV camera 12 or solid state image sensor 45 is converted into the digital signal by means of the A/D converter, but the analog image signal may be directly stored in an analog type optical or magnetic disc device.

In the above embodiments, the two images are viewed from the endoscope at the two different positions, but it is also possible to take more than two images. Then, it may be expected to obtain the distance, height and depressions and protrusions in a much more precise manner.

In the above embodiments, the bending section of the endoscope is moved by rotating the angle handle 20 arranged in the operation section which is provided at the proximal end of the insertion section. It is also possible to rotate the rotary drum by means of an electric motor. In such a case, operation members such as switches and variable resistors may be provided in the operation section of the endoscope or in a light source unit to which the endoscope is coupled. In the latter case, the bending section may be moved in a remote control manner.

As explained above in detail, according to the invention, a plurality of endoscopic images viewed from different positions are taken together with the information representing the mutual relation of these images and these signals are processed to derive various kinds of information about the geometrical property of the object.

What is claimed is:

1. A method of processing endoscope images taken by an endoscope having an insertion section, a bending section provided at a distal end of the insertion section and an operation section for controlling a movement of the bending section, comprising the steps of:

entering a first endoscopic image of an object taken by the endoscope situated in a first position;

entering a second endoscopic image of the object taken by the endoscope situated in a second position; said second endoscopic image being at least partially overlapped with said first endoscopic image; and detecting a positional relation between said first and second positions of the endoscope.

2. A method according to claim 1, wherein said first and second endoscopic images are taken by moving the bending section of the endoscope.

3. A method according to claim 2, wherein said bending section of the endoscope is moved by actuating an operation member provided in the operation section which is provided at a proximal end of the insertion section of the endoscope, and said positional relation is detected by detecting a movement of said operation member.

4. A method according to claim 3, wherein said bending section is moved by rotating an angle handle provided in the operation section, said angle handle being coupled with said bending section via an angle wire, and the positional relation is detected by detecting a rotation of said angle handle.

5. A method according to claim 4, wherein said positional relation is detected by detecting a rotation of a pattern disc coupled coaxially with the angle handle.

6. A method according to claim 5, wherein the rotation of said pattern disc is detected by a photoelectric sensor.

7. A method according to claim 4, wherein said positional relation is detected by detecting the movement of the angle wire on which a pattern is provided.

8. A method according to claim 2, wherein said bending section is bent at a single position such that a direction of an optical axis of an objective lens provided in a distal end of the bending section with respect to the object is changed.

9. A method according to claim 2, wherein said bending section is bent at two positions such that a direction of an optical axis of an objective lens provided in a distal end of the bending section with respect to the object is remained unchanged.

10. A method of processing endoscopic images taken by an endoscope having an insertion section, a bending section provided at a distal end of the insertion section, and an operation section for controlling a movement of the bending section, comprising the steps of:

entering a first endoscopic image of an object taken by the endoscope in a first position;

entering a second endoscopic image of the object taken by the endoscope in a second position, said second endoscopic image being at least partially overlapped with said first endoscopic image;

detecting a positional relation between said first and second endoscopic images; and processing said first and second endoscopic images in accordance with said positional relation to derive geometric information of the object.

11. A method according to claim 10, wherein said processing step comprises a step of deriving a shift amount represented by a distance between corresponding two points on the first and second endoscopic images.

12. A method according to claim 11, wherein said distance is detected by deriving a correlation between small regions in the first and second endoscopic images.

13. A method according to claim 12, wherein prior to deriving the correlation, distortion of the first and second endoscopic images is corrected.

14. A method according to claim 13, wherein after the distortion of the endoscopic images has been corrected, the endoscopic images are subjected to an interpolation.

15. A method according to claim 14, wherein said interpolation is carried out in accordance with a b-spline function.

16. A method according to claim 12, wherein said correlation is detected with the aid of an electronic correlation calculator.

17. A method according to claim 16, wherein said step of detecting the correlation comprises a step of deriving correlation values of first regions in the first and second endoscopic images, a step of selecting first regions whose correlation values exceed a predetermined threshold value, a step of deriving correlation values of second regions which are smaller than said first regions in selected first regions, a step of detecting a second region having the maximum correlation value, and a step of deriving an address of the second region having the maximum correlation value.

18. A method according to claim 16, wherein said correlation is calculated in accordance with the following equation, $$\frac{\overline{f \cdot g} - \overline{f} \cdot \overline{g}}{\sigma_f \cdot \sigma_g}$$

wherein f·g is an average of a product of the first and second images f and g, e,ovs/f/ ·e,ovs/g/ is a product of an average of f and a average of g, and $\sigma_f$ and $\sigma_g$ are standard deviations of the images f and g.

19. A method according to claim 12, wherein prior to deriving the correlation, the first and second endoscopic images are subjected to a spatial frequency filtering.

20. A method according to claim 12, wherein each of said first and second endoscopic images is subjected to Fourier transformation and spatial frequency filtering, successively, and output signals derived by the spatial frequency filtering are multiplied, and a multiplied signal is subjected to inverse Fourier transformation.

21. A method according to claim 19 or 20, wherein said spatial frequency filtering is carried out by extracting high frequency components of the first and second endoscopic images.

22. A method according to claim 21 wherein the high frequency components are extracted with the aid of a Laplacian filter.

23. A method according to claim 19 or 20, wherein said spatial frequency filtering is effected by extracting low frequency components in the first and second endoscopic images.

24. A method according to claim 23, wherein the low frequency components are extracted with the aid of an averaging filter.

25. A method according to claim 16, wherein the correlation value C is derived by the following equation;

$$C = F^{-1}\left(\frac{F \cdot G^*}{|F||G|}\right)$$

wherein $F^{-1}$ represents the inverse Fourier transformation, F and G* are Fourier transformations of the first and second endoscopic images and |F| and |G| are absolute values of F and G*.

26. A method according to claim 12, wherein said correlation is detected with the aid of an optical correlation calculator.

27. A method according to claim 26, wherein the step of detecting the distance comprises producing a holographic film containing a part of the first endoscopic image, forming a superimposed image of an image of a part of said holographic film and of an image of a part of the second endoscopic image, and detecting a position of a point having maximum light intensity in said superimposed image.

28. A method according to claim 27, wherein said holographic film is produced by projecting an image of said part of the first endoscopic image borne on a photographic film onto a raw photographic film together with reference light, and by developing the raw photographic film to provide said holographic film.

29. A method according to claim 27, wherein said holographic film is produced by displaying an incoherent image of the first endoscopic image on a display device, converting the incoherent image into a coherent image, projecting a part of the coherent image onto a raw photographic film together with reference light, and developing the raw photographic film to provide said holographic film.

30. A method according to claim 11, wherein said processing step comprises a step of calculating a height of a relevant point of the object in accordance with the shift amount.

31. A method according to claim 11, wherein said processing step comprises a step of calculating a distance between two points on the object in accordance with the shift amount.

32. A method according to claim 10, further comprising a step of displaying the first and second endoscopic images, a gray image representing depressions and protrusions of the object, and a three dimensional image of the object.

33. A method according to claim 32, wherein said displaying step comprises displaying a distance between two points on a displayed image, said points being indicated by cursors.

34. A method according to claim 32, wherein said displaying step comprises displaying a height of a point on a displayed image, said point being denoted by a cursor.

* * * * *